US00PP28976P3

(12) United States Plant Patent
Danziger

(10) Patent No.: US PP28,976 P3
(45) Date of Patent: Feb. 20, 2018

(54) ***OCIMUM* PLANT NAMED 'DBASBLOOM'**

(50) Latin Name: *Ocimum basilicum*
Varietal Denomination: DBASBLOOM

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 100 days.

(21) Appl. No.: 14/998,626

(22) Filed: Jan. 20, 2016

(65) Prior Publication Data

US 2017/0208723 P1 Jul. 20, 2017

(51) Int. Cl.
*A01H 5/02* (2006.01)

(52) U.S. Cl.
USPC ..... Plt./258

(58) Field of Classification Search
USPC ..... Plt./258
See application file for complete search history.

*Primary Examiner* — Anne M Grunberg
(74) *Attorney, Agent, or Firm* — Cassandra Bright

(57) ABSTRACT

A new and distinct *Basilicum* cultivar named 'DBASBLOOM' is disclosed, characterized by full structure, compact habit with prolonged flowering. Additionally, the cultivar has sepals and flower stalks of purple color. The new variety is a *Basilicum,* normally produced as an outdoor garden or container plant.

2 Drawing Sheets

Figure 1:
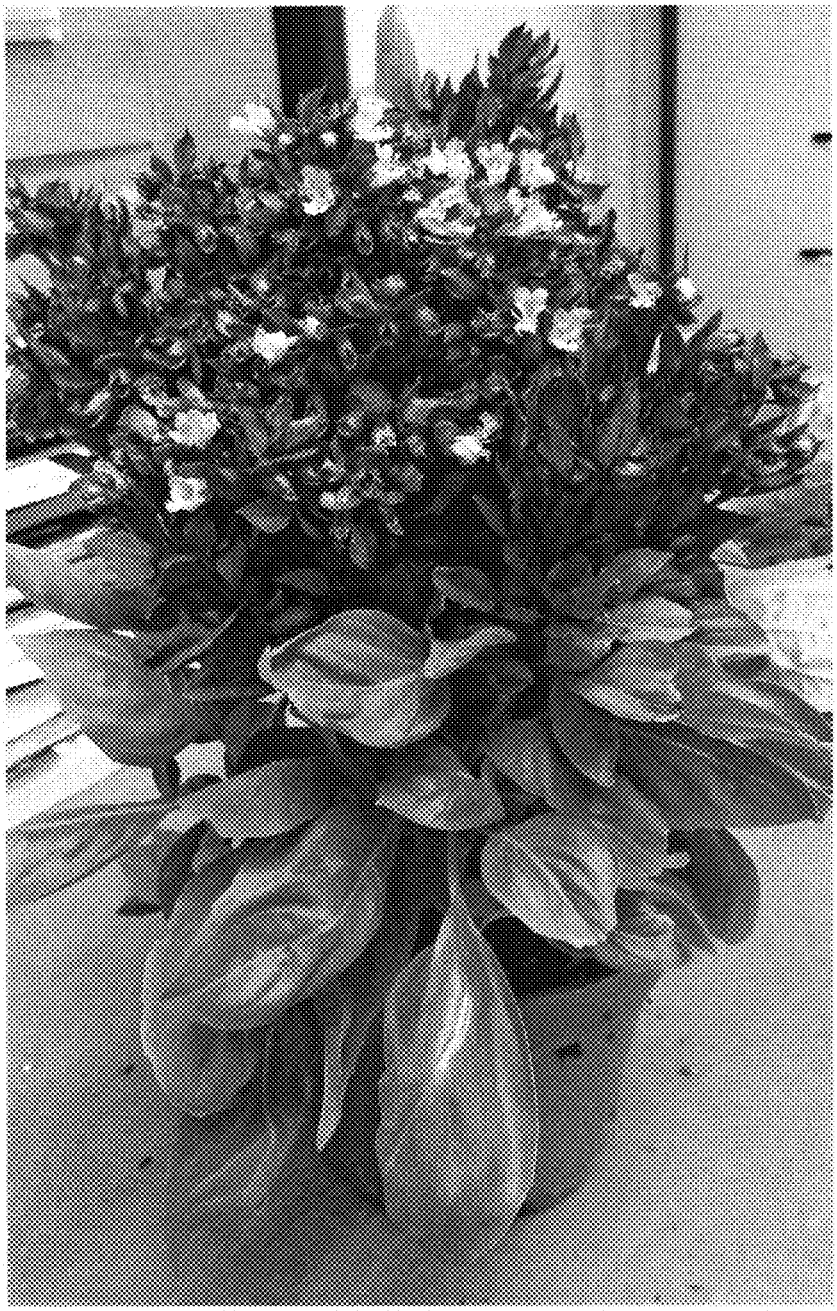

Latin name of the genus and species: *Ocimum basilicum.*
Variety denomination: 'DBASBLOOM'.

BACKGROUND OF THE INVENTION

The new *Ocimum basilicum* cultivar is the product of a planned breeding program conducted by the inventor, Gavriel Danziger, in Moshav Mishmar Hashiva, Israel. The objective of the breeding program was to produce novel *Ocimum* varieties for ornamental commercial applications. The open pollination resulting in this new variety was made during 2010.

The seed parent is the proprietary variety referred to as *Ocimum* 'BS-12-3'. The pollen parent is unknown as it was an open pollination breeding program. The new variety was discovered 16 Jul. 2012 by the inventor in a group of seedlings resulting from the March 2012 open pollination in an open field in Moshav Mishmar Hashiva, Israel.

Asexual reproduction of the new cultivar was performed by vegetative cuttings. This was first performed at a research greenhouse in Moshav Mishmar Hashiva, Israel in July of 2011 and has shown that the unique features of this cultivar are stable and reproduced true to type in 15 successive generations.

SUMMARY OF THE INVENTION

The cultivar 'DBASBLOOM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBASBLOOM'. These characteristics in combination distinguish 'DBASBLOOM' as a new and distinct *Basilicum* cultivar:

1. Compact plant habit.
2. Full plant structure.
3. Purple shade of the sepals.

4. Purple shade of the flower stalks.
5. Prolonged flowering.

Plants of the new cultivar 'DBASBLOOM' are similar to plants of the seed parent, *Ocimum* 'BS-12-3' in most horticultural characteristics, however, plants of the new cultivar 'DBASBLOOM' differ in the following;

1. New variety is more compact than the seed parent variety.
2. New variety is fuller, with more branches than the seed parent variety
3. The new variety flowers more abundantly than the seed parent.

COMMERCIAL COMPARISON

Plants of the new cultivar 'DBASBLOOM' are comparable to the unpatented commercial variety *Ocimum* 'Magic Mountain'. The two varieties are similar in most horticultural characteristics; however, the new variety 'DBASBLOOM' differs in the following:

1. Plants of 'DBASBLOOM' are shorter (25 cm) than 'Magic Mountain' (65 cm).
2. Plants of 'DBASBLOOM' are narrower (20-25 cm) than 'Magic Mountain' (30 cm).

Plants of the new cultivar 'DBASBLOOM' can also be compared to the unpatented commercial variety *Ocimum basilicum* 'Habana' (U.S. Plant Pat. No. 24,643 P3). The two *Ocimum* varieties are similar in most horticultural characteristics; however, the new variety 'DBASBLOOM' differs in the following:

1. Plants of 'DBASBLOOM' are shorter (25 cm) than 'Habana' (50 cm).
2. 'DBASBLOOM' leaf is longer (6 cm) than the leaves of 'Habana' (3.5 cm).
3. 'DBASBLOOM' has purple shades on stems compared to green shades of the stems of 'Habana'.

BRIEF DESCRIPTION OF THE PHOTOGRAPHS

The accompanying photograph in FIG. 1 illustrates in full color a typical flowering plant of 'DBASBLOOM' grown in a greenhouse, in a 13 cm pot. Age of the plant photographed is approximately 15 weeks from a rooted cutting.

Figure 2:
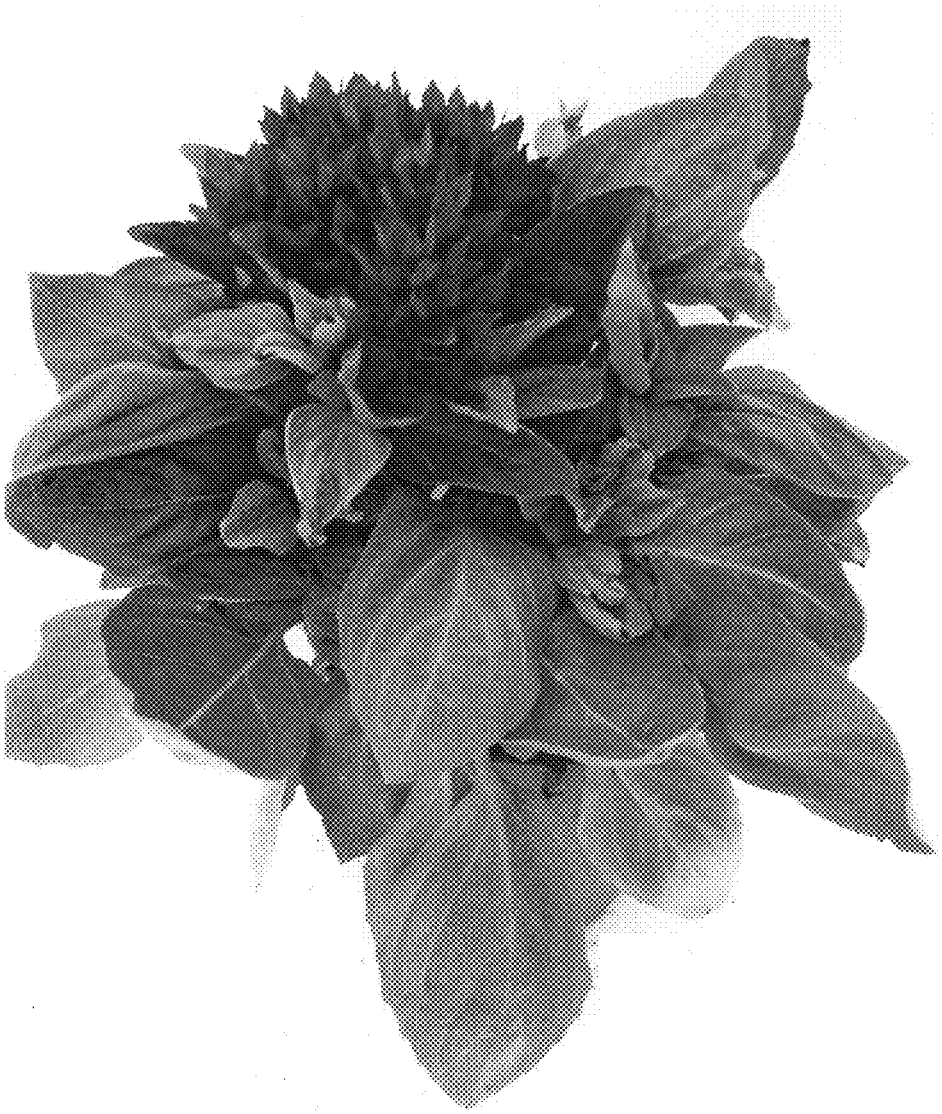

FIG. 2 illustrates plant post-flowering, with persistent sepals.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DBASBLOOM' plants grown in the Autumn, to Spring in moderate climate in a greenhouse, in Moshav Mishmar Hashiva, Israel. The growing temperature ranged from 20° C. to 30° C. during the day and from 16° C. to 25° C. during the night. General light conditions are bright, normal sunlight. Measurements and numerical values represent averages of typical plant types.

Botanical classification: *Ocimum basilicum* 'DBASBLOOM'.

PROPAGATION

Type of propagation typically used: Vegetative cutting.

Time to initiate roots: 7 days at approximately 24° C.

Time to produce a rooted cutting: About 14 days at 24° C.

PLANT

Age of plant described: Approximately 15 weeks.

Container size of the plant described: 13 cm.

Overall plant shape or growth habit: Compact and upright; umbel inflorescence gives mounded appearance.

Length of primary lateral branches: Approximately 20 to 25 cm.

Diameter of lateral branches: Approximately 0.2 to 0.3 cm.

Quantity of lateral branches: Approximately 25 to 30.

Branch color: Near RHS Purple N77D; darker at tips near RHS Purple N77B.

Branch texture/pubescence: Very short and sporadically occuring in the base of internodes.

Internode length: Approximate average 1.5 cm.

FOLIAGE

Leaf:

*Arrangement*.—Whorled.

*Quantity*.—Approximately 10 per main branch.

*Average length*.—Approximately 6 cm, lateral occuring. Basal leaves that are significantly longer, around 9-10 cm. In addition there are very small leaves just below the inflorescence that are significantly shorter, around 1-1.5 cm.

*Average width*.—Approximately 3.5 cm. Basal leaves that are significantly wider, around 6 cm. In addition there are very small leaves prior to the inflorescence that are significantly narrower, around 1-1.5 cm).

*Shape of blade*.—Elliptic.

*Apex*.—Slightly acute.

*Base*.—Attenuate.

*Attachment*.—Petiolate.

*Margin*.—Entire.

*Texture of top surface*.—Smooth.

*Texture of bottom surface*.—Smooth.

*Aspect of leaf blade*.—Variable, foliage can be convex, or concave. Typically entire surface moderately undulating as well.

*Plant leaf color*.—Young foliage upper side: Near RHS Yellow-Green group 146B. Young foliage under side: Near RHS Yellow-Green group 146C. Mature foliage upper side: Near RHS Green N137C. Mature foliage under side: Near RHS Green N138 B.

*Venation*.—Type: Reticulate. Venation color upper side: Near RHS Green N138B. Venation color under side: Near RHS Green N138D.

*Petiole*.—Average Length: Approximately 1.5-2 cm. Basal leaf petiole around 5 cm. Diameter: Approximately 0.15 cm. Color: Near RHS Yellow-Green 146D.

FLOWER

Natural flowering season: From spring to autumn in moderate Mediterannean climate.

Inflorescence type and habit: Terminal inflorescence, the cymes structure is thyrse.

Flower longevity on plant: About 4 days from mature bud to fade flower. One whole inflorescence continuously blooms for 6 to 8 weeks.

Quantity of flowers: About 18 blooming spikes per plant with 4 open flowers in each spike.

Inflorescence size:

*Diameter*.—Approximately 5 cm.

*Height*.—Approximately 5 cm.

*Flowers and buds per inflorescence*.—Average of 4 flowers and 4 buds per inflorescence.

Inflorescence leaf color:

*Young foliage upper side*.—Near RHS Purple N77A.

*Young foliage under side*.—Near RHS Grey-Purple N187A.

*Mature foliage upper side*.—Near RHS Grey-brown N199A.

*Mature foliage under side*.—Near RHS Grey-brown N199A.

*Venation*.—Type: Reticulate. Venation color upper side: Near RHS Grey-Purple N187C. Venation color under side: Near RHS Grey-Purple N187D.

*Petiole*.—(Refers to the very small leaves which appear prior to the inflorescence, from which the flowers will later bloom, these leaves are permanent. These leaves have significantly shorter petiole.). Average Length: Approximately 0.2 cm. Diameter: Approximately 0.1 cm. Color: Near RHS Grey-Purple N187A.

Peduncle:

*Length*.—0.2 cm.

*Diameter*.—0.1 cm.

*Texture*.—Smooth.

*Color*.—Near RHS Purple N79B.

*Orientation*.—About 45° upward-facing branch.

*Strength*.—Medium.

*Petal arrangement*.—The corolla is sympetalous and typically bilabiate with 4 small, highly fused lobes forming an upper lip and 1 oblong lower lip.

Individual flowers:

*Size*.—Diameter: Approximately 0.5 cm. Length: Approximately 0.8 to 1.0 cm.

*Persistence*.—Persistent.

*Fragrance*.—Licorice scent.

Petals:

*Margin*.—Lower lip is gently scalloped and upper lip is entire, divided to 4 lobes.

*Tip shape*.—Upper lip: The tip of the 4 lobes of is blunt (truncate). Lower lip: Rounded, slightly acute.

*Length*.—Upper lip: 0.5 cm. Lower lip: 0.7 cm. Tube: 0.4 cm.

*Width*.—Upper lip: 0.6 cm. Lower lip: 0.4 cm. Tube: 0.2 cm.

*Texture*.—Upper lip: Smooth, slightly ribbed longwise. Lower lip: Smooth, slightly ribbed longwise. Tube: Smooth.

Color: Upper Lip.

*When opening*.—Inner surface: The 2 central lobes are near RHS Purple 77A and 77B, and the 2 lateral lobes are near RHS Purple 75D. Outer surface: The 2 central lobes are near RHS Purple 77A and 77B, and the 2 lateral lobes are near RHS Purple 75D.

*Fully opened*.—Inner surface: Near RHS Purple 75A. Outer surface: Near RHS Purple 75A.

*Fading*.—Inner surface: Near RHS Purple 77B. Outer surface: Near RHS Purple 77A.

Color: Lower Lip.

*When opening*.—Inner surface: Near RHS White 155C. Outer surface: Near RHS Green-White 157B.

*Fully opened*.—Inner surface: Near RHS White 155C. Outer surface: Near RHS Green-White 157D.

*Fading*.—Inner surface: Near RHS White 155A. Outer surface: Near RHS White 155A.

Color: Tube.

*When opening*.—Inner surface: Near RHS White NN155C. Outer surface: Near RHS White N155A.

*Fully opened*.—Inner surface: Near RHS White NN155C. Outer surface: Near RHS White N155A.

*Fading*.—Inner surface: Near RHS White NN155C. Outer surface: Near RHS White N155A.

Bud:

*Shape*.—Ovate.

*Length*.—0.7 cm.

*Diameter*.—0.3 cm.

*Color*.—Body: Near RHS Green-White 157A. Tip: Near RHS Purple group 77C.

Sepals:

*Shape*.—Quantity per flower: 5 highly fused sepals.

*Length*.—Approximately 0.5 cm.

*Width*.—Approximately 0.1 to 0.2 cm.

*Margin*.—Entire.

*Texture*.—Ribbed longwise.

*Color*.—Near RHS Grey-green 197A changing to near RHS Grey-purple 185 B toward tips.

REPRODUCTIVE ORGANS

Stamens:

*Number*.—4.

*Filament length*.—Approximately 0.5 to 0.7 cm.

Anthers:

*Shape*.—Elliptical.

*Length*.—Approximately 0.1 cm.

*Color*.—Near RHS Yellow-White 158C.

*Pollen*.—Color: Near RHS Yellow-White 158D. Quantity: Scant.

Pistil:

*Number*.—1.

*Length*.—Approximately 1.0 cm.

*Style*.—Length: Approximately 0.8 cm. Color: Near RHS Red-Purple 72B.

Stigma:

*Shape*.—Curved V-shape.

*Color*.—Near RHS White group N155B.

Ovary color: Near RHS Yellow-Green 1C.

OTHER CHARACTERISTICS

Seeds and fruits: None observed to date.

Disease/pest resistance: Specimen has shown resistance to diseases common to *Ocimum*.

What is claimed is:

1. A new and distinct cultivar of *Ocimum basilicum* plant named 'DBASABLOOM as herein illustrated and described.

* * * * *